United States Patent [19]

Sugiyama et al.

[11] Patent Number: 5,221,690

[45] Date of Patent: Jun. 22, 1993

[54] INCREASING THE CHOROIDAL BLOOD FLOW

[75] Inventors: Tetsuya Sugiyama; Satoru Tokuoka, both of Osaka; Masayuki Nakajima, Kyoto; Ikuo Azuma, Hyogo, all of Japan

[73] Assignee: R-Tech Ueno Ltd., Osaka, Japan

[21] Appl. No.: 867,359

[22] Filed: Apr. 13, 1992

[30] Foreign Application Priority Data

Oct. 2, 1991 [JP] Japan .................................. 3-255125

[51] Int. Cl.$^5$ ..................... A61K 31/19; A61K 31/557
[52] U.S. Cl. ...................................... 514/573; 514/912
[58] Field of Search ................................ 514/573, 912

[56] References Cited

U.S. PATENT DOCUMENTS 5,001,153  3/1991  Ueno et al. ........................... 514/530
5,114,971  5/1992  Stjernschantz et al. ............ 514/530

FOREIGN PATENT DOCUMENTS 289349  4/1988  European Pat. Off. .
308135  9/1988  European Pat. Off. .

Primary Examiner—Frederick E. Waddell
Assistant Examiner—Kimberly R. Jordan
Attorney, Agent, or Firm—Sughrue, Mion, Zinn, Macpeak & Seas

[57] ABSTRACT

A method for increasing the choroidal blood flow which comprises administering to a subject in need of such increasing a 13,14-dihydro-15-keto-20-ethyl-prostaglandin F, a pharmaceutically acceptable salt thereof or a lower alkyl ester thereof.

3 Claims, 1 Drawing Sheet

INCREASING THE CHOROIDAL BLOOD FLOW

BACKGROUND OF THE INVENTION

1. Field of the Invention

The present invention relates to a treatment for increasing the choroidal blood flow using 13,14-dihydro-15-keto-20-ethyl-prostaglandin Fs, salts or lower alkyl esters thereof.

2. Background Information

The compounds used in the present invention, i.e. 13,14-dihydro-15-keto-20-ethyl-prostaglandin Fs, salts or lower alkyl esters thereof are known compounds and described in EP-A-289349 (particularly in Examples 7, 11, 12, 13, 14 and 24) and EP-A-308135 (particularly in Example 8). In the former publication, the compounds are described as having a blood pressure increasing activity and in the latter publication, the compounds are described as having an ocular hypotensive activity. Nothing has been reported, however, about an activity of the above compounds on the choroidal blood flow. As a result of a study about the biological activity of 13,14-dihydro-15-keto-20-ethyl-prostaglandin Fs, salts or lower alkyl esters thereof, it has now been discovered that these compounds have an activity of increasing choroidal blood flow.

SUMMARY OF THE INVENTION

In a first aspect, the present invention provides a method for increasing the choroidal blood flow which comprises administering to a subject in need of such increasing a 13,14-dihydro-15-keto-20-ethyl-prostaglandin F, a pharmaceutically acceptable salt thereof or a lower alkyl ester thereof.

In a second aspect, the present invention provides a use of a 13,14-dihydro-15-keto-20-ethyl-prostaglandin F, a pharmaceutically acceptable salt thereof or a lower alkyl ester thereof for the manufacture of a medicament for increasing choroidal blood flow.

In a third aspect, the present invention provides a pharmaceutical composition for increasing choroidal blood flow comprising a 13,14-dihydro-15-keto-20-ethyl-prostaglandin F, a pharmaceutically acceptable salt thereof or a lower alkyl ester thereof in association with a pharmaceutically acceptable carrier, diluent or excipient.

The present invention also provides a process for preparing the medicament or the pharmaceutical composition which comprises combining a 13,14-dihydro-15-keto-20-ethyl-prostaglandin F, a pharmaceutically acceptable salt thereof or a lower alkyl ester thereof with a pharmaceutically acceptable carrier, diluent or excipient.

BRIEF DESCRIPTION OF THE DRAWING

The FIGURE of he drawing plots the results of Test Example 1 of the application, namely time versus relative choroidal blood flow.

DETAILED DESCRIPTION OF THE INVENTION

Figure 1:
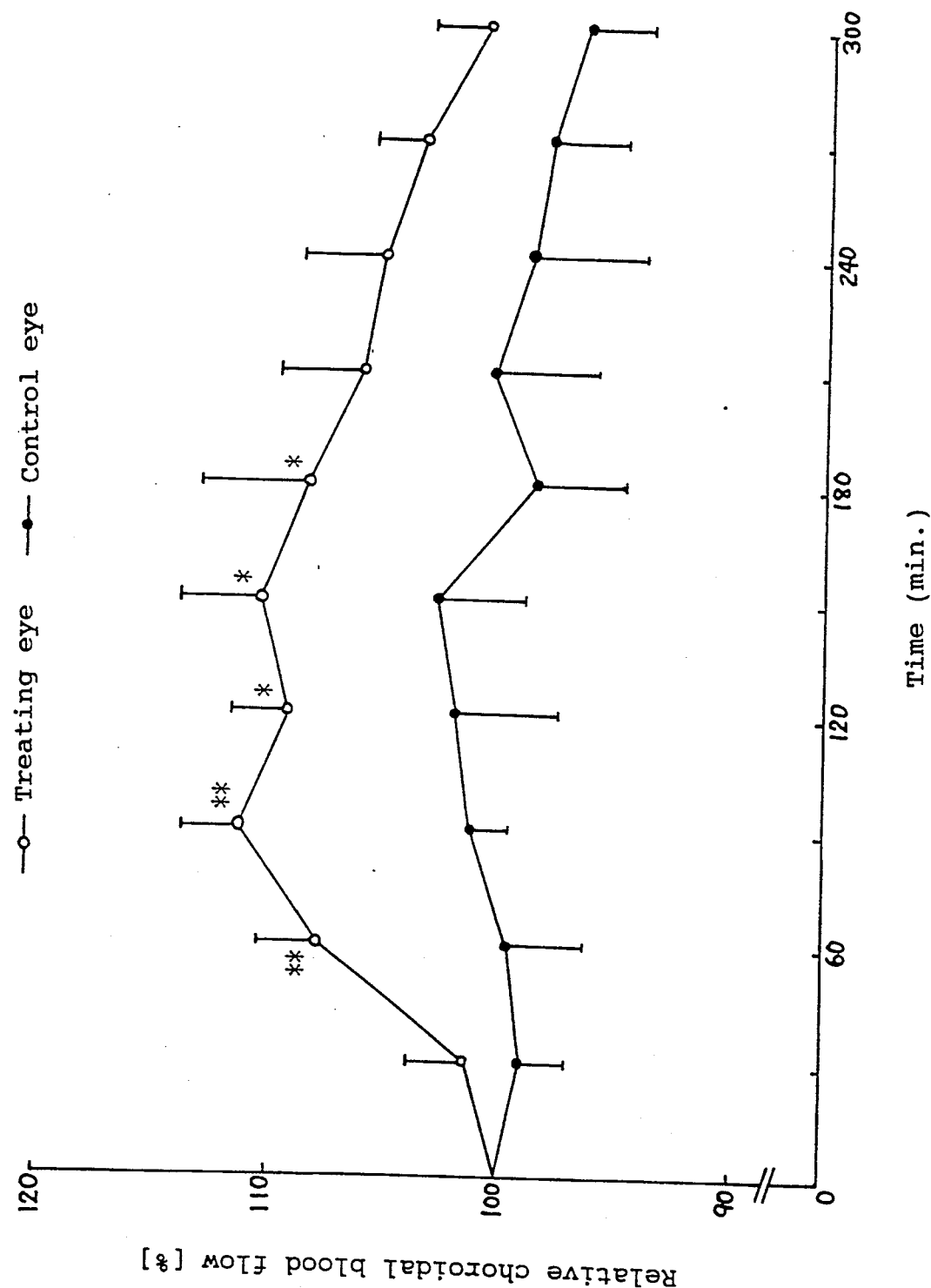

The compounds used as the active ingredient in the present invention are compounds having basic structure of the natural prostaglandin F and having a saturated carbon to carbon bond between positions 13 and 14, lacking the hydroxyl group at position 15, having an oxo group instead of said hydroxy group at position 15 and having an omega chain elongated by combining an ethyl group at position 20 (i.e. the terminal of the omega chain), and salts or lower alkyl esters thereof.

The term "prostaglandin F" herein includes prostaglandin $F_1\alpha$, $F_2\alpha$ and $F_3\alpha$.

The salts of 13,14-dihydro-15-keto-20-ethyl-prostaglandin Fs are conveniently pharmaceutically acceptable salts.

Suitable "pharmaceutically acceptable salts" includes conventional non-toxic salts, and may be a salt with an inorganic base, for example a metal salt such as an alkali metal salt (e.g. sodium salt, potassium salt, etc.) and an alkaline earth metal salt (e.g. calcium salt, magnesium salt, etc.), ammonium salt, a salt with an organic base, for example, an amine salt (e.g. methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, procaine salt, caffeine salt, etc.), a basic amino acid salt (e.g. arginine salt, lysine salt, etc.), tetraalkylammonium salt and the like. These salts can be prepared by the conventional process, for example from the corresponding acid and base or by salt interchange.

The term "lower alkyl" in lower alkyl esters means alkyl groups having 1 to 6, preferably 1 to 4 carbon atoms, and include for example, methyl, ethyl, propyl, isopropyl, butyl, isobutyl, tert-butyl, pentyl, hexyl etc.

Among the compounds used in the present invention, methods for the preparation of 13,14-dihydro-15-keto-20-ethyl-prostaglandin $F_2\alpha$ and its methyl ester, ethyl ester, isopropyl ester and n-butyl ester are described in Examples 24, 7, 11, 12 and 13 of EP-A-289,349, respectively. A method for the preparation of the isopropyl ester is also described in Example 7 of EP-A-30,135. A method for the preparation of 13,14-dihydro-15-keto-20-ethyl-prostaglandin $F_1\alpha$ methyl ester is described in Example 14 of EP-A-289,349. Other compounds can be prepared analogously taking into consideration the other processes known for the preparation of prostaglandin compounds.

Choroid (Chorioidea) is the tissue present between the sciera and the retina with rich pigment and vascular, extending from the optic disk to the ora serrata. It is composed of four layers: supra-choroid (*Stratum perichorioideum*), layer of vessels (Lamina *vasculosa*), choriocapillaries (*Lamina choriocapillaris*) and Bruch's membrane (*Lamina vitrea*).

Since the compounds used in the invention have an activity of increasing choroidal blood flow, the compounds used in the invention, or medicaments or pharmaceutical compositions comprising said compounds, are useful in the treatment of, for example, ischemic disorder of choroid such as ischemic choroidal syndrome.

Such activity can be measured by the conventional pharmacological assays which have been used for evaluating the blood flow. The term "treatment" herein refers to any means of control of a disease including preventing the disease, curing the disease, relieving the disease and arresting or relieving the development of the disease.

The compounds used in the present invention may be used as a medicine for animals and human beings and usually applied systemically or locally by such methods as ophthalmic administration, oral administration, intravenous injection (including instillation), subcutaneous injection, suppository and the like. While the dosage will vary depending on the particular animal or human patient, age, body weight, symptom to be treated, desired therapeutic effect, administration route, term of treatment and the like, satisfactory effects will be obtained with the dosage of 0.01–100 μg/eye administered locally or 0.001–500 mg/kg administered systemically in 2 to 4 divided doses a day or as a sustained form.

The ophthalmic composition used according to the invention includes ophthalmic solution, ophthalmic ointment and the like. The ophthalmic solution can be prepared by dissolving an active ingredient in a sterile aqueous solution such as a physiological saline or a buffered solution, or as a combination of a solid and a solution for dissolving said solid to make a ready-to-use preparation. The ophthalmic ointment can be prepared by mixing an active ingredient with an ointment base.

The solid composition for oral administration used according to the invention includes tablets, troches, buccals, capsules, pills, powders, granules and the like. The solid composition contains one or more active substances in admixture with at least an inactive diluent, e.g. lactose, mannitol, glucose, hydrocypropyl cellulose, fine crystalline cellulose, starch, polyvinyl pyrolidone, magnesium aluminate metasilicate. The composition may contain additives, in addition to the inactive diluent, for example, lubricants e.g., magnesium stearate, a disintegrator e.g. cellulose calcium gluconates, stabilizers e.g. $\alpha$-, $\beta$-, or $\gamma$-cyclodextrins, etherated cyclodextrins (e.g. dimethyl-$\alpha$-, dimethyl-$\beta$-, trimethyl-$\beta$-, or hydroxypropyl-$\beta$-cyclodextrins), branched cyclodextrins (e.g. glucosyl- or maltosyl-cyclodextrins), formyl cyclodextrins, sulfur-containing cyclodextrins, misoprotols or phospholipids. Such cyclodextrins may increase the stability of the compounds by forming an inclusion compounds. The stability may be often increased by forming lyposome with phospholipids. Tablets and pills may be coated with an enteric or gastroenteric film e.g. white sugar, gelatin, hydroxypropylcellulose, hydroxypropylmethylcellulose phthalates and the like, if necessary, and furthermore they may be covered with two or more layers. Additionally, the composition may be in the form of capsules made of substance easily absorbed e.g. gelatin. The composition may be in the form of buccals, when an immediate effect is desired. For this purpose, base e.g. glycerine, lactose may be used.

Liquid compositions for oral administration include pharmaceutically acceptable emulsions, solutions, suspensions, syrups, elixirs and the like and contain a commonly used inactive diluent e.g. purified water or ethyl alcohol. The composition may contain additives e.g. wetting agents, suspending agents, sweeteners, flavors, perfumes and preservatives.

The composition of the present invention may be in the form of sprays which may contain one or more active ingredients and which can be prepared according to a well known methods.

An injection of this invention for non-oral administration includes sterile aqueous or nonaqueous solutions, suspensions, and emulsions. Diluents for the aqueous solution or suspension include, for example, distilled water for injection, physiological saline and Ringer's solution. Diluents for the nonaqueous solution and suspension include, for example, propylene glycol, polyethylene glycol, vegetable oils e.g. olive oil, alcohols, e.g. ethanol and polysorbates. The composition may contain other additives, e.g. preservatives, wetting agents, emulsifying agents, dispersing agents and the like. These are sterilized by filtration through, e.g. a bacteria- retaining filter, compounding with a sterilizer, gas sterilization or radiation sterilization. These can be prepared by producing a sterilized water or a sterilized solvent for injection before use.

Another formulation according to the present invention is a rectal or vaginal suppository. This can be prepared by mixing at lest one active compound according to the invention with a suppository base e.g. cacao butter and optionally containing nonionic surfactant for improving absorption.

A more complete understanding of the present invention can be obtained by reference to the following Formulation Examples and Test Examples which are provided herein for purpose of illustration only and are not intended to limit the scope of the invention.

FORMULATION EXAMPLE 1

Powders for injection

|  | (Parts by weight) |
| --- | --- |
| 13,14-dihydro-15-keto-20-ethyl-prostaglandin $F_2\alpha$ | 1 |
| mannitol | 5 |
| distilled water | 0.4 |

The above ingredients are mixed, stirred, sterilized, filtered and lyophilized to give powders for injection.

FORMULATION EXAMPLE 2

Injectable solution

|  | (Parts by weight) |
| --- | --- |
| 13,14-dihydro-15-keto-20-ethyl-prostaglandin $F_2\alpha$ methyl ester | 0.2 |
| nonion surfactant | 2 |
| distilled water | 98 |

The above ingredients are mixed and sterilized to give and injectable solution.

FORMULATION EXAMPLE 3

Powders for oral administration

|  | (Parts by weight) |
| --- | --- |
| 13,14-dihydro-15-keto-20-ethyl-prostaglandin $F_2\alpha$ ethyl ester | 5 |
| light anhydrous silicic acid | 5 |
| Abicel TM | 20 |
| lactose | 70 |

The above ingredients are mixed to give powders for oral administration.

FORMULATION EXAMPLE 4

Soft gelatin capsules

|  | (Parts by weight) |
| --- | --- |
| 13,14-dihydro-15-keto-20-ethyl-prostaglandin $F_2\alpha$ propyl ester | 1 |
| Panasate TM | 899 |

The above ingredients are mixed and filled in soft gelatine capsules.

FORMULATION EXAMPLE 5

Ophthalmic solution

|  | (Parts by weight) |
|---|---|
| 13,14-dihydro-15-keto-20-ethyl-prostaglandin F$_2\alpha$ isopropyl ester | 1 |
| Physiological saline | 10 |

The above ingredients are placed in separate vials. The vials are combined for preparing a solution on actual use.

In the above formulation Examples, the active ingredient can be replaced by any other compound within the compounds used in the invention.

TEST EXAMPLE 1

Six normal white rabbits (weight: 2.1-3.2 kg) were anesthetized by intraperitoneal administration of urethane (1.3 mg/kg). After 2 hours, experiments were conducted under stable depth of anesthesia (room temperature : 25° C). The blood flow was measured by a heat gradient tissue blood flowmeter (thermostromuhr ?) BTG-221 (Biomedical Science). Thus, an embedding type thermodiffusion sensor TGD-8R was fixed on the underlying membrane of Tenon capsule at a position between the medial rectus muscle and the superior rectus muscle and distanced by 10 mm from the Dimbus. The tissue blood flow was measured continuously by an amplifier TGA-2. One eye was used as the treating eye and the other was used an the control. The treating eye received 50 μl of 0.06% aqueous solution of 13,14-dihydro-15-keto-20-ethyl-prostaglandin F$_2\alpha$ isopropyl ester and the control eye received 50 μl of the physiological saline. Change in the tissue blood flow was measured over 5 hours.

The results are shown in Table 1 and also plotted in the Figure, wherein * denotes $p<0.05$ and ** denotes $p<0.01$, according to the paired t-test (n=6, vs. control eye).

TABLE 1

| Time (min.) | Rabbit |  |  |  |  |  |
|---|---|---|---|---|---|---|
|  | A | B | C | D | E | F |
| (Treating eye) | | | | | | |
| 30 | 100 | 103 | 97 | 102 | 104 | 102 |
| 60 | 108 | 108 | 103 | 108 | 111 | 109 |
| 90 | 114 | 112 | 107 | 110 | 113 | 111 |
| 120 | 113 | 110 | 108 | 107 | 110 | 107 |
| 150 | 116 | 108 | 107 | 108 | 113 | 110 |
| 180 | 117 | 105 | 105 | 106 | 110 | 107 |
| 210 | 112 | 103 | 102 | 105 | 108 | 106 |
| 240 | 111 | 103 | 101 | 105 | 107 | 104 |
| 270 | 105 | 101 | 101 | 105 | 106 | 103 |
| 300 | 100 | 98 | 99 | 104 | 103 | 101 |
| (control eye) | | | | | | |
| 30 | 102 | 98 | 97 | 98 | 101 | 98 |
| 60 | 105 | 98 | 96 | 99 | 102 | 98 |
| 90 | 104 | 100 | 99 | 101 | 102 | 101 |
| 120 | 110 | 99 | 98 | 100 | 103 | 101 |
| 150 | 112 | 100 | 98 | 101 | 102 | 103 |
| 180 | 105 | 97 | 94 | 97 | 98 | 99 |
| 210 | 108 | 98 | 96 | 100 | 97 | 102 |
| 240 | 108 | 96 | 95 | 98 | 96 | 99 |
| 270 | 104 | 96 | 95 | 98 | 97 | 98 |
| 300 | 102 | 95 | 95 | 96 | 96 | 95 |

(Values are shown in % taking the value at 0 minute as 100%.)

The above results clearly show that the compound used in the present invention had as activity increasing choroidal blood flow.

We claim:

1. A method for increasing the choroidal blood flow which comprises administering to a subject in need of such increasing a 13,14-dihydro-15-keto-20-ethyl-prostaglandin F, a pharmaceutically acceptable salt thereof or a lower alkyl ester thereof, in an amount effective to increase the choroidal blood flow.

2. A method according to claim 1, wherein the 13,14-dihydro-15-keto-20-ethyl-prostaglandin is a 13,14-dihydro-15-keto-20-ethyl-prostaglandin F$_2\alpha$.

3. A method according to claim 1, wherein the lower alkyl ester is isopropyl ester.

* * * * *